United States Patent [19]

Kaiser et al.

[11] Patent Number: 4,769,368
[45] Date of Patent: Sep. 6, 1988

[54] 2,3,4,8,9,9A-HEXAHYDRO-4-ARYL-1H-INDENO(1,7-CD)AZEPINES

[75] Inventors: Carl Kaiser, Haddon Heights, N.J.; Hye-Ja Oh, Cheltenham; Joseph Weinstock, Phoenixville, both of Pa.

[73] Assignee: SmithKline Beckman Corporation, Philadelphia, Pa.

[21] Appl. No.: 827,681

[22] Filed: Feb. 10, 1986

[51] Int. Cl.$^4$ .................. A61K 31/55; C07D 223/32
[52] U.S. Cl. ..................................... 514/217; 540/586
[58] Field of Search ...................... 540/586; 514/217

[56] References Cited

U.S. PATENT DOCUMENTS

| | | | |
|---|---|---|---|
| 4,104,379 | 8/1978 | Gallagher, Jr. et al. | 540/586 X |
| 4,111,957 | 9/1978 | Holden et al. | 540/586 X |
| 4,197,297 | 4/1980 | Weinstock | 424/244 |
| 4,284,555 | 8/1981 | Gold et al. | 269/239 |

FOREIGN PATENT DOCUMENTS 5330 11/1979 ............................................ 223/16

0088575 2/1983 European Pat. Off. .

OTHER PUBLICATIONS

Chemical Abstracts, vol. 79, No. 5, Aug. 6, 1973.
Chemical Abstracts, vol. 84, No. 7, Feb. 16, 1976.
Flaim, K. E. et al., *Binding of a Novel Dopaminergic Agonist Radioligand [$^3H$]-Fenoldopam$^1$(SK&F 82526) to D-1 Receptors in Rat Striatum*, Life Sci., 36:1427–36 (1985).
Van Rooyen, J. M. and J. Offermeier, *Peripheral Dopaminergic Receptors*, S. Afr. Med. J., 59:329-32 (1981).

*Primary Examiner*—Donald G. Daus
*Assistant Examiner*—William A. Teoli, Jr.
*Attorney, Agent, or Firm*—Vincent L. Fabiano; Stuart R. Suter; Alan D. Lourie

[57] ABSTRACT

2,3,4,8,9,9a-Hexahydro-4-aryl-1H-indeno[1,7-cd;]-azepines are selective dopamine receptor site binding agents.

8 Claims, No Drawings

2,3,4,8,9,9A-HEXAHYDRO-4-ARYL-1H-INDENO(1,7-CD)AZEPINES

This invention relates to a new series of compounds which are 2,3,4,8,9,9a-hexahydro-4-aryl-1H-indeno[1,7-cd]azepines optionally substituted at the 6,7-positions. The compounds are specific binding agents for $D_1$-dopamine receptor sites with little binding at $D_2$-dopamine receptor sites. As described more fully below, this series of compounds has either agonist or antagonist activity at the $D_1$-sites.

BACKGROUND OF THE INVENTION

The benzazepine compounds in the art exemplify both dopamine D-site agonists, or dopaminergic, compounds as well as dopamine D-site antagonists.

For example, fenoldopam is the prototype peripheral dopaminergic agent which has $D_1$ and some $D_2$ agonist activity (U.S. Pat. No. 4,197,297). This compound has been described to have renal dilating, anti-hypertensive, anti-shock and anti-congestive heart failure activity.

Representative of the dopamine antagonistic agents are the compounds disclosed in EP No. 5,298 and 5,300 as well as Y. Itoh et al., Eur. J. Pharmacol. 100 119 (1984). Such compounds are described to have neuroleptic or antidepressant activity.

The DA, or D, receptor sites at which the compounds of this invention have been found to work are linked to adenylate cyclase in the body. Specificity of action at these receptors is a desired biological property; J. M. van Rossum et al., S. Afr. Med. J. 59 329 (1981); K. E. Flaim et al., Life Sciences, 36 1427 (1985).

The compounds of this invention have a novel ring system in their structures and also have a novel specificity of biological activity.

DESCRIPTION OF THE INVENTION

The compounds of this invention are represented by the following structural formula:

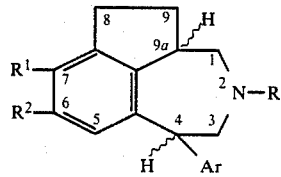

in which:
Ar is furyl, thienyl, phenyl or phenyl which is substituted by one or two methoxy, hydroxy, halo or methyl groups;
R is hydrogen, allyl or $C_{1-4}$-alkyl; and,
$R^1$ and $R^2$ are, each, hydrogen, $C_{1-4}$-alkoxy, hydroxy, halo or trifluoromethyl, at least one of $R^1$ and $R^2$ being other than hydrogen.
"∼" at the 9a, 4 positions of formula I denotes the isomeric positions of the hydrogen attached thereto.

Subgeneric groups of the compounds of formula I are: (1) the compounds in which Ar is phenyl or 4'-hydroxy-phenyl and $R^1$ and $R^2$ are both hydroxy. (2) the compounds in which Ar is phenyl or 4'-hydroxyphenyl and R is hydrogen. (3) the compounds in which one of $R^1$ and $R^2$ is chloro and the other hydroxy.

Also included in this invention are the pharmaceutically acceptable, acid addition salts formed with acids such as methanesulfonic, hydrochloric, hydrobromic, hydriodic, sulfamic, nitric, sulfuric, phosphoric, maleic, tartaric, acetic, ethanedisulfonic acids. The salt forms of these compounds are easily prepared by reacting the base form of formula I with at least one stoichiometric quantity of acid in an inert organic or aqueous solvent system. The salts are isolated and purified by standard methods. $C_{2-6}$-Alkanoyl ester derivatives may also be prepared at any hydroxy group at positions 6, 7 or in Ar by methods known in the benzazepine art.

The compounds of formula I are prepared by the following reaction sequence (A):

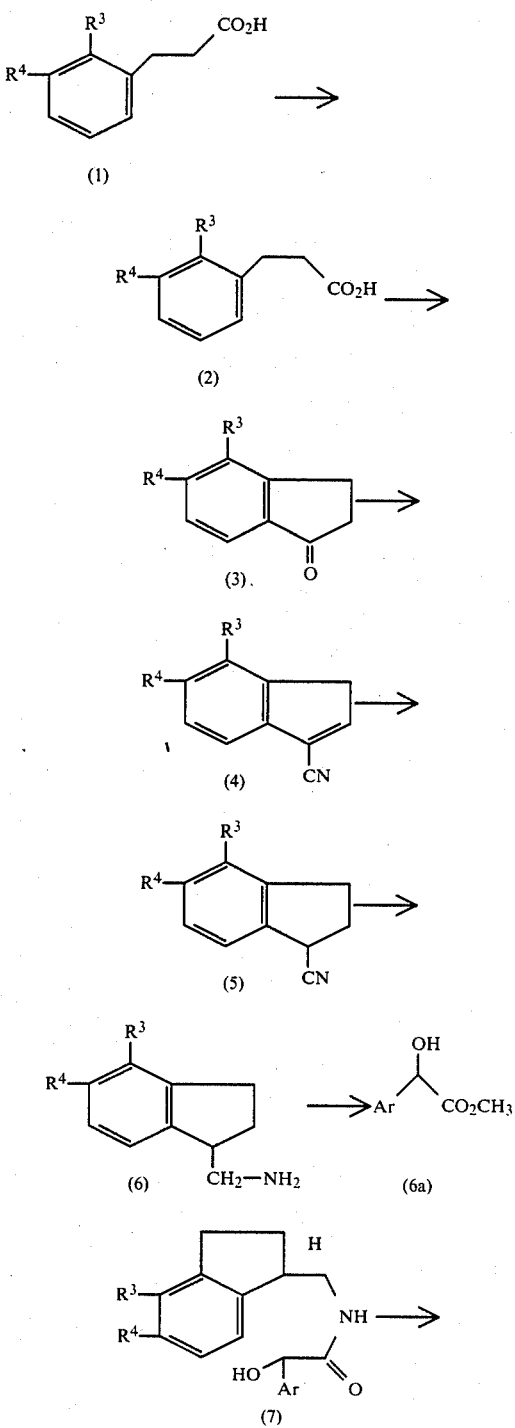

-continued

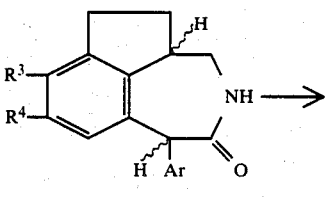

(8)

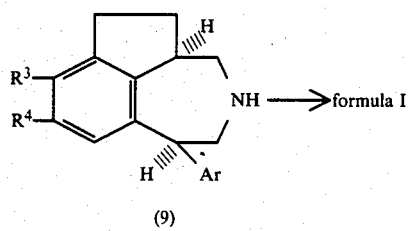

(9)

in which Ar is as defined above and $R^3$ and $R^4$ are as defined above for $R^1$ and $R^2$ except that the substituent must be stable under reaction conditions of the sequence or be present in precursor or protected form for later generation of the $R^1$ and $R^2$ substituents of formula I.

The reaction sequence (A) involves three major parts: the preparation of a 1-aminomethyl-4,5-disubstituted indan (1→6); formation of the desired 6,7-disubstituted 2,3,4,8,9,9a-hexahydro-4-aryl-1H-indeno[1,7-cd]azepine ring (6 8); optional N-alkylation and removal of the 3-oxo and any protective groups (8 formula I).

One key intermediate, the 1-aminomethyl-4,5-substituted indan (6), is prepared conveniently by reacting the indanone (3) with trimethylsilyl cyanide to form the 1-cyanohydrin ester. After 1,2-dehydration, the double bond and the cyano centers are reduced to give the desired 1-aminomethylindan (6).

An optionally substituted arylglycolic ester (6a) is reacted under heating with the 1-aminomethylindan to give the amide (7). This is cyclized using polyphosphoric acid to give the 4-aryl-2,3,4,8,9,9a-hexahydro-1H-indeno[1,7-cd]azepin-3-one (8). The 3-keto compound is converted to the desired indenoazepine (9) by reaction with an amide reducing agent such as lithium aluminum hydride or diborane in tetrahydrofuran-ether at reflux temperature until the reduction is complete.

One skilled in the art will recognize that the compounds of this invention can exist as cis, trans isomers at the 1,5-positions or as optical isomers due to the presence of two chiral centers. These isomers are all part of this invention and are separated by methods well known in the art. Often, separation of the isomers is carried out most conveniently at the protected intermediate stage, such as compound (9) or one of its N-alkylated congeners. We have isolated the cis and trans isomers of one species of this invention and assigned configurations on the basis of NMR and X-ray crystallographic studies. The cis isomers have preferred biological activity.

Finally, the third aspect of the synthetic sequence involves optional N-alkylation using a reactive ester, preferably a chloride, bromide or iodide, in the presence of an excess of an acid binding agent such as pyridine, triethylamine or dimethylaniline. Removal of any protecting groups, such as lower alkoxy groups, from the 4-aryl or nuclear benz- rings is accomplished by reaction with an ether cleaving agent, for example boron tribromide or trichloride, preferably in a halogenated organic solvent for example methylene chloride, carbon tetrachloride or chloroform; pyridine hydrochloride; aqueous hydrogen bromide; aluminum chloride or bromide in a suitable solvent for example benzene or carbon disulfide; hydriodic acid; hydrogen fluoride-antimony pentafluoride; or trifluoromethylsulfonic acid in thioanisole to give the preferred hydroxy substituted compound of formula I.

The compounds of Formula I have potent $D_1$-binding activities with low $D_2$-binding When the $R^1$ substituent at the 7-position is a halo, such as chloro, bromo, iodo or fluoro, or a trifluoromethyl and $R^2$ is hydroxy or lower alkoxy, the compounds are $D_1$-dopamine antagonists. As such, they have neuroleptic, anti-depressant and anti-aggressive activity.

When the $R^1$ and $R^2$ substituents at the 6,7-position are hydroxy or lower alkoxy groups, the compounds are $D_1$-dopamine agonists. As such the compounds have the activity of a specific dopamine-like compound which induces peripheral dopaminergic activity which is manifested in renal dilating activity, anti-hypertensive activity or relief of the symptoms of congestive heart failure. The compounds which are centrally active are also useful in treating the symptoms of Parkinson's disease. The compounds of formula I which have $D_1$-agnostic activity, that is those in which $R^1$ and $R^2$ are hydroxy, are preferred because of their potent and selective spectra of biological activity.

As an example of the $D_1$-dopamine specificity of the compounds of this invention, a species of formula I, 6,7-dihydroxy-2,3,4,8,9-9a-hexahydro-4-phenyl-1H-indeno[1,7-cd]azepine hydrobromide, was submitted to standard binding tests for $D_1$ and $D_2$-dopamine sites, see K. Flaim, loc. cit. for testing protocols.

| Displacement of | cis | trans |
|---|---|---|
| [$^3$H] fenoldopam rat caudate ($D_1$) ($K_B$) | 24 ± 5 nM | 1220 nM |
| [$^3$H] spiroperidol bovine pituitary ($D_2$) | 14% at $10^{-5}$ M | 0% at $10^{-5}$ M |

The cis isomer is very potent and selective for the $D_1$ dopamine sites. The cis isomers of formula I are preferred aspects of this invention.

The pharmaceutical compositions of this invention having dopamine site binding activity are prepared in conventional dosage unit forms by incorporating a compound of formula I, an isomer or a pharmaceutically acceptable acid addition salt or ester derivative thereof, with a nontoxic pharmaceutical carrier according to accepted procedures in a nontoxic amount sufficient to produce the desired pharmacodynamic activity in a subject, animal or human. Preferably the compositions will contain the active ingredient in an active but nontoxic amount selected from 0.1-100 mg/kg preferably about 0.3-50 mg/kg of active ingredient per dosage unit but this quantity depends on the relative potency of the basic compound, the specific biological activity desired, the route of administration and the condition of the patient. Oral dosage forms are of prime importance here, preferably selected from the dosage unit ranges given above. Intravenous or subcutaneous doses would be lower.

The method of inducing $D_1$-dopaminergic binding activities in human or animal patients comprises administering a nontoxic quantity of the compound of formula I as described above, which is sufficient to induce $D_1$ activity, to said patient in need of such treatment internally, that is, orally, rectally, parenterally or transcutaneously. For example, a composition as described above is administered from 1-4 times daily. The clinical dysfunctions outlined above are the objects of the methods of treatment of this invention. Compounds of formula I in which $R^1$ is halo or trifluoromethyl and $R^2$ is hydroxy or lower alkoxy are dopamine $D_1$ antagonists; those in which $R^1$ and $R^2$ are both hydroxy or lower alkoxy are dopamine $D_1$ agonists. Generally speaking, the compounds of formula I in which R is hydrogen are most suitable at peripheral receptor sites; those in which R is allyl or lower alkyl are most suitable at either peripheral or central receptor sites.

The pharmaceutical carrier employed may be, for example, either a solid or liquid. Exemplary of solid carriers are lactose, terra alba, sucrose, talc, gelatin, agar, pectin, acacia, magnesium stearate, stearic acid, and the like. Exemplary of liquid carriers are syrup, peanut oil, olive oil, water and the like. Similarly, the carrier or diluent may include any time delay material well known to the art, such as glyceryl monostearate or glyceryl distearate alone or with a wax. Such sustained release products as well as derivatives which may be gradually metabolized to the active parent can be employed to prolong the unique biological activity of the compounds of this invention.

A wide variety of pharmaceutical forms can be employed. Thus, if a solid carrier for oral administration is used the preparation can be tableted, placed in a hard gelatin capsule in powder, regular or sustained release pellet form, in the form of a troche or lozenge. The amount of solid carrier will vary widely but preferably will be from about 25 mg to about 1 g. If a liquid carrier is used, the preparation will be in the form of a syrup, emulsion, soft gelatin capsule, sterile injectable liquid such as an ampul, or an aqueous or nonaqueous liquid suspension.

The pharmaceutical preparations are made following the conventional techniques of the pharmaceutical chemist involving mixing, granulating and compressing when necessary, or variously mixing and dissolving the ingredients as appropriate to give the desired end product.

The following examples are designed solely to illustrate the preparation and use of the compounds of this invention. The temperatures are centigrade. Other variations of these examples will be obvious to those skilled in the art.

EXAMPLE 1

2,3-Dimethoxycinnamic acid (50 g, 0.24 m) was suspended in a mixture of 120 ml of ethanol and 40 ml of glacial acetic acid, then treated with 0.8 g of 10% palladium-on-charcoal. The mixture was warmed on a steam bath before putting on the Paar shaker. Hydrogenation was continued until the uptake of hydrogen stopped (45 minutes). The catalyst was filtered off and the resulting filtrate was evaporated to dryness. The resulting residue solidified on standing. A quantitative yield of the desired 2,3-dimethoxyphenylpropionic acid was isolated.

2,3-Dimethoxycinnamic acid can be purchased or is prepared by the condensation of 2,3-dimethoxybenzaldehyde and malonic acid in the presence of pyridine [Org. Syn. Coll., Vol. 4 732 (1963)].

2,3-Dimethoxyphenylpropionic acid (17.5 g, 0.083 m) was mixed with 200 g of polyphosphoric acid, then heated on a steam bath for 15 minutes until the reaction mixture became homogeneous and color became red. The mixture was cooled and poured into ice-water. The resulting solid was collected. The crude product was redissolved in ether, washed with water, 5% sodium bicarbonate solution and brine. The extract was dried and evaporated to give white crystalline 4,5-dimethoxyindan-1-one; 11.6 g (72.5%); recrystallized from ether; m.p. 71°-3°

The indanone (30.7 g, 0.156 m) was dissolved in 650 ml of methylene chloride and treated with 2.1 g of zinc iodide. Trimethylsilyl cyanide (18.5 g, 0.187 m) was added slowly under nitrogen then the mixture was refluxed for 6 hours, and cooled to room temperature. The mixture was poured into ice-water carefully. Chloroform was added for extraction. The organic layer was washed with brine and dried. The extract was evaporated to give a semi-solid which was dissolved in 500 ml of toluene, filtering off the insoluble material (4 g; not characterized). The extract was treated with 43 ml of trifluoroacetic acid and refluxed for 2 hours, then cooled and diluted with ether, washed with water, 5% sodium bicarbonate, water, brine and dried.

Evaporating gave the crude product which was purified over a dry silica column, eluting with a mixture of ether and n-hexane (3:2). The product was 10.8 g (34.5%) of 3-cyano-6,7-dimethoxy-1H-indene. An analytical sample was prepared by recrystallization from ethyl acetate-n-hexane; m.p. 107°-9°.

Anal Calc'd. for $C_{12}H_{11}NO_2$: C, 71.63; H, 5.51; N, 6.97. Found: C, 71.57; H, 5.59; N, 6.81.

The nitrile (5 g) was suspended in 150 ml of ethanol then treated with 0.5 g of 10% palladium-on-charcoal (moistened with ethyl acetate) and slightly warmed on a steam bath. The mixture was hydrogenated on a Parr apparatus for 30 minutes. Catalyst was filtered off and the filtrate was evaporated to give the 1-cyanoindan.

An analytical sample was prepared by recrystallization from ethanol; m.p. 68°-70°.

Anal. Calcd. for $C_{12}H_{13}NO_2$: C, 70.92; H, 6.45; N, 6.89. Found: C, 70.84; H, 6.48; N, 6.87.

The nitrile (9 g, 0.044 m), dissolved in a mixture of 200 ml of ether and 50 ml of tetrahydrofuran, was added slowly to a lithium aluminum hydride (6.7 g) suspension in 200 ml of ether and 50 ml of tetrahydrofuran keeping gentle reflux. After the addition, the mixture was refluxed for 5 hours. The crude 1-aminomethyl-4,5-dimethoxyindan was converted to the hydrochloride salt, 5.0 g (47%). An analytical sample was prepared by recrystallization from methanol; m.p. 214°-7°.

Anal. Calcd. for $C_{12}H_{17}NO.HCl$: C, 59.14; H, 7.44; N, 5.75. Found: C, 58.79; H, 7.43; N, 5.88.

1-Aminomethyl-4,5-dimethoxyindan (4.75 g, 0.023 m) was mixed with 3.8 g (0.023 m) of methyl mandelate and heated in an oil bath (100°) overnight under nitrogen. The residue was dissolved in methylene chloride, then insoluble material was removed. The desired product was separated by dry silica column chromatography, eluting with a mixture of 3% methanol in methylene chloride. The eluant gave a brown syrup upon evaporation, the open chain amide. This was mixed with 100 g of polyphosphoric acid and heated on a steam bath for 30 minutes, then poured into ice-water. The resulting solid was collected, dissolved in methylene chloride, washed with water, brine and dried. Evaporation gave white cyclic amide which was washed with methanol to give 2.4 g (32%) of product. An analytical sample was prepared by recrystallizing from methanol-ethyl acetate; m.p. 204°-8°.

Anal. Calcd. for $C_{20}H_2NO_3$: C, 74.28; H, 6.55; N, 4.33. Found: C, 73.87; H, 6.72; N, 4.21.

The cyclic amide (2.3 g, 0.0071 m) was suspended in a mixture of 50 ml of tetrahydrofuran and 150 ml of ether and was added to 1.1 g (0.03 m) of lithium aluminum hydride suspended in 100 ml of ether. The mixture was refluxed for 4 hours and worked up as described above. TLC (silica, 5% MeOH-95% $CH_2Cl_2$) showed two spots close together. A maleate salt was made, m.p. 164°-6°, 1.36 g (45%) but no separation of products was obtained. The salt was converted back to free base (10% NaOH-EtOAc). The cis and trans isomers of 6,7-dimethoxy-2,3,4,8,9,9a-hexahydro-4-phenyl-1H-indeno[1,7-cd]azepine base were separated via flash silica column chromatography, eluting with 3% methanol-97% methylene chloride-0.25% conc. ammonia. High $R_f$ spot as the HCl salt: 0.4 g, mp 240°-2°.

Low $R_f$ spot as the HCl salt: 0.55 g, mp 225°.

| | Anal. Calcd. for $C_{20}H_{23}NO_2 \cdot HCl$: | |
|---|---|---|
| | Calcd. | Found (high $R_f$) | Found (low $R_f$) |
| C: | 69.45 | 69.30 | 69.43 |
| H: | 6.99 | 7.05 | 7.08 |
| N: | 4.05 | 4.12 | 4.10 |

Nuclear magnetic resonance (NMR) and crystal studies demonstrated the low $R_f$ fraction was the cis isomer and the high $R_f$ fraction was the trans isomer.

EXAMPLE 2

The 6,7-dimethoxy cis isomer from Example 1 (0.24 g, 0.00078 m) was dissolved in 6 ml of methylene chloride and cooled to 0°. Boron tribromide (3.15 ml of a 1 g/5 ml stock solution) was added slowly. The mixture was stirred in the same ice-bath for 2 hours during which period the mixture reached room temperature. It was cooled again and methanol was added slowly. The mixture was evaporated to dryness. The residue was washed with ether and triturated with acetonitrile to give 25 g (89%) of cis-6,7-dihydroxy-2,3,4,8,9,9a-hexahydro-4-phenyl-1H-indeno[1-7-cd]azepine hydrobromide which was recrystallized from methanol ether; m.p. 290°.

Anal. Calcd. for $C_{18}H_{19}NO_2 \cdot HBr$: C, 59.68; H, 5.56; N, 3.87. Found: C, 59.89; H, 5.73; N, 3.87.

EXAMPLE 3

The same procedure was used on the trans-6,7-dimethoxy isomer (0.25 g, 0.00824 m) as was described for the cis-isomer in Example 2. Elemental analysis and a mass spectrum of the product (0.16 g) indicated that sample was contaminated with ring brominated product, therefore, the contaminated product was dissolved in 10 ml of methanol and treated with 100 mg of 10% palladium-on-charcoal. The mixture was hydrogenated for 5 hours. The catalyst was removed and the filtrate was evaporated. The residue was dissolved in methanol and ether was added to separated trans-6,7-dihydroxy-2,3,4,8,9,9a-hexahydro-4-phenyl-1H-indeno[1,7-cd]azepine hydrobromide; m.p. 210°; no m/e=360 (brominated product) observed.

Anal. Calcd for $C_{18}H_{19}NO_2 \cdot HBr \cdot \frac{1}{2}H_2O$: C, 58.23; H, 5.70; N, 3.77; Br, 21.52. Found: C, 58.35; H, 5.78; N, 3.76; Br, 21.58.

EXAMPLE 4 cis-6,7-Dimethoxy-2,3,4,8,8,9a-hexahydro-4-phenyl-1H-indeno[1,7-cd]azepine (0.3 g) in 10 ml of acetonitrile is mixed with 0.3 ml (0.002 m) of triethylamine and 0.14 ml (0.0011 m) of allyl bromide. The mixture is heated at 85°-95° for 2½ hours. The reaction mixture is evaporated. The residue is suspended in water and extracted twice with ethyl acetate. The organic extract is washed with water, brine and evaporated to give the cis-6,7-dimethoxy-3-allyl compound.

This material is dissolved in 10 ml of methylene chloride and cooled to −15° at which time 0.6 ml of boron tribromide in 40 ml of methylene chloride is added slowly over ¼ hour. The reaction mixture is stirred at room temperature for 3 hours, cooled and treated with an excess of methanol slowly and with cooling. The methanol is evaporated to give a residue. This is dissolved in a minimum amount of methanol and cooled. Evaporation and crystallization gives cis-2-allyl-6,7-dihydroxy-2,3,4,8,9,9a-hexahydro-4-phenyl-1H-indeno[1,7-cd]azepine hydrobromide, m.p. 195°-199° (dec.).

An aliquot of the hydrobromide (100 mg) in aqueous methanol is neutralized using sodium carbonate solution. The base is reacted with a slight excess of methanesulfonic acid in methanol to give the methanesulfonate salt.

EXAMPLE 5

1-Aminomethyl-4,5-dimethoxyindan (2.0 g, 0.01 m) and methyl p-methoxymandelate (1.8 g, 0.01 m) is heated at 125° under nitrogen for 16 hours. The mixture is purified over a silica column to give the intermediate amide.

The amide (1.3 g) is heated with 25 g of polyphosphoric acid for 1 hour, quenched and the product extracted from the reaction mixture to give cis, trans-6,7-dimethoxy-2,3,4,8,8,9a-hexahydro-4-(4-methoxyphenyl)-1H-indeno[1,7-cd]azepin-3-one.

This compound (750 mg) is reacted with an excess of lithium aluminum hydride in ether-tetrahydrofuran at reflux for 8 hours. After working up as described above, the two isomers of the 6,7,4'-trimethoxy intermediate are isolated as the hydrochloride salts.

A mixture of 275 mg of cis-6,7-dimethoxy-2,3,4,8,9,9a-hexahydro-4-(4-methoxyphenyl)-1H-indeno[1,7-cd]azepine and 15 ml of 48% hydrobromic acid is heated at reflux overnight. The reaction mixture is evaporated in vacuo. The residue is purified over a silica column to obtain cis-6,7-dihydroxy-2,3,4,8,9,9a-hexahydro-4-(4-hydroxyphenyl)-1H-indeno[1,7-cd]azepine hydrobromide.

In similar fashion but using boron tribromide demethylation as described above, the following compounds are prepared:

trans-6,7-dihydroxy-2,3,4,8,9,9a-hexahydro-4-(3,4-dichlorophenyl)-1H-indeno[1,7-cd]azepine hydrochloride;

cis, trans-6,7-dihydroxy-2,3,4,8,9,9a-hexahydro-4-(3-methylphenyl)-1H-indeno[1,7-cd]azepine;

cis-6,7-difluoro-2,3,4,8,9,9a-hexahydro-4-(4-hydroxyphenyl)-1H-indeno[1,7-cd]azepine hydrochloride;

cis-trans-6-hydroxy-2,3,4,8,9,9a-hexahydro-4-(2-thienyl)-1H-indeno[1,7-cd]azepine hydrobromide.

EXAMPLE 6

1-Methylaminomethyl-4-chloroindan (19.5 g, 0.1 m), prepared as above but using either chemical or poisoned sodium borohydride reduction conditions is condensed with ethyl mandelate as described above. The resulting crude amide is cyclized by heating in an excess of polyphosphoric acid. The cyclic amide (7.8 g) is treated with lithium aluminum hydride to give cis-7-chloro-2-methyl-2,3,4,8,9,9a-hexahydro-4-phenyl-1H-indeno[1,7-cd]azepine base and hydrochloride.

Similarly, cis, trans-7-trifluoromethyl-2-methyl-2,3,4,6,8,9,9a-hexahydro-4-phenyl-1H-indeno[1,7-cd]azepine hydrobromide, cis-7-chloro-6-hydroxy-2-methyl-2,3,4,6,8,9,9a-hexahydro-4-(2-furyl)-1H-indeno[1,7-cd]azepine hydrochloride are prepared.

EXAMPLE 7

Using the methods described above and starting with 1-aminomethyl-5-bromo-4-methoxyindan, 7-bromo-6-methoxy-2,3,4,8,9,9a-hexahydro-4-phenyl-1H-indeno[1,7-cd]azepine is prepared. This intermediate is N-methylated using formic acid-formaldehyde to give cis, trans-7-bromo-6-methoxy-2-methyl-2,3,4,8,9,9a-hexahydro-4-phenyl-1H-indeno[1,7-cd]azepine hydrobromide and, after demethylation using boron tribromide, cis or trans-7-bromo-6-hydroxy-2-methyl-2,3,4,8,9,9a-hexahydro-4-phenyl-1H-indeno[1,7-cd]azepine.

EXAMPLE 8

| Ingredients | Mg per Capsule |
| --- | --- |
| cis-6,7-Dihydroxy-2,3,4,8,9,9a-hexahydro-4-phenyl-1H—indeno-[1,7-cd]azepine hydrobromide | 15 (free base) |
| Magnesium stearate | 2 |
| Lactose | 200 |

The above ingredients are thoroughly mixed and placed into hard gelatin capsules. Such capsules are administered orally to subjects in need of treatment from 2-5 times daily to induce $D_1$-dopaminergic activity to treat hypertension.

EXAMPLE 9

| Ingredients | Mg per Capsule |
| --- | --- |
| cis-2-Methyl-7-chloro-2,3,4,8,9,9a-hexahydro-4-phenyl-1H—indeno-[1,7-cd]azepine hydrochloride methanesulfonate | 10 (free base) |
| Corn starch | 30 |
| Polyvinyl pyrrolidone | 12 |
| Corn Starch | 16 |
| Magnesium stearate | 3 |

The first two ingredients are thoroughly mixed and granulated. The granules obtained are dried, mixed with the remaining corn starch and magnesium stearate, and compressed into scored tablets which can optionally be broken in two for 5 mg dosages for $D_1$-antagonist activity.

Sustained release capsules may be prepared by using the methods of U.S. Pat. No. 2,738,303. Of course one such capsule may replace several conventional tablets or capsules.

The capsules or tablets thusly prepared are administered orally to an animal or human requiring stimulation or inhibition of $D_1$-dopamine receptors within the dose ranges set forth hereinabove. Similarly other compounds of formula I and the illustrative examples can be formulated in the same manner to give pharmaceutical compositions useful in the methods of this invention based on their chemical characteristics and relative biological activity using the test methods outlined.

What is claimed is:

1. A chemical compound of the structural formula:

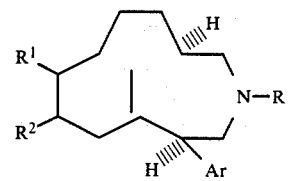

in which:
Ar is furyl, thienyl, phenyl or phenyl which is substituted with 1 to 2 methoxy, hydroxy, halo or methyl groups;
R is hydrogen, allyl or $C_{1-4}$-alkyl;
$R^1$ is halo, trifluoromethyl, hydroxy, or lower alkoxy; and
$R^2$ is hydroxy or lower alkoxy; or a pharmaceutically acceptable acid addition salt thereof.

2. The cis isomer of a compounds of claim 1.

3. The compound of claim 1 in which $R^1$ is halo or trifluoromethyl and $R^2$ is hydrogen or hydroxy.

4. The compound of claim 1 in which R is $C_{1-4}$-alkyl.

5. The compound of claim 1 being cis-6,7-dihydroxy-2,3,4,8,9,9a-hexahydro-4-phenyl-1H-indeno[1,7-cd]azepine or a pharmaceutically acceptable acid addition salt thereof.

6. The compound of claim 1 being cis-7-bromo-6-hydroxy-2l-methyl-2,3,4,8,9,9a-hexahydro-4-phenyl-1H-indeno[1,7-cd]azepine or a pharmaceutically acceptable acid addition salt.

7. A pharmaceutical composition having $D_1$-dopamine binding activity comprising a nontoxic, active therefor quantity of a compound of claim 1 combined with a pharmaceutical carrier.

8. A pharmaceutical composition having $D_1$-dopamine antagonist activity comprising a nontoxic, acitve therefor quantity of a compound of claim 3 combined with a pharmaceutical carrier.

* * * * *

UNITED STATES PATENT AND TRADEMARK OFFICE
CERTIFICATE OF CORRECTION

PATENT NO.  : 4,769,368
DATED       : Sep. 6, 1988
INVENTOR(S) : Carl Kaiser et al.

It is certified that error appears in the above-identified patent and that said Letters Patent is hereby corrected as shown below:

Claim 1: Replace the structural formula with the following structural formula:

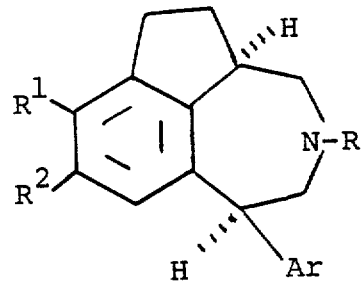

and at line 31:   "to" should read  ... or ...

Claim 6, Li. 47:   "hydroxy-21-methyl should read ... hydroxy-2-methyl ...

Signed and Sealed this

Twenty-ninth Day of August, 1989

Attest:

DONALD J. QUIGG

Attesting Officer

Commissioner of Patents and Trademarks